(12) United States Patent
Cabilly et al.

(10) Patent No.: US 7,122,104 B2
(45) Date of Patent: Oct. 17, 2006

(54) ELECTROPHORESIS APPARATUS FOR SIMULTANEOUS LOADING OF MULTIPLE SAMPLES

(75) Inventors: Shmuel Cabilly, Gedera (IL); Uri Yogev, Herzelin (IL); Ilana Margalit, Ramat Gan (IL)

(73) Assignee: Ethrog Biotechnology, Ltd., Ness Ziona (IL)

( * ) Notice: Subject to any disclaimer, the term of this patent is extended or adjusted under 35 U.S.C. 154(b) by 441 days.

(21) Appl. No.: 10/370,459

(22) Filed: Feb. 24, 2003

(65) Prior Publication Data

US 2003/0121783 A1    Jul. 3, 2003

Related U.S. Application Data

(63) Continuation of application No. 09/651,087, filed on Aug. 30, 2000, now Pat. No. 6,562,213.

(51) Int. Cl.
*G01N 27/447* (2006.01)
*G01N 27/453* (2006.01)
*C12M 1/34* (2006.01)

(52) U.S. Cl. .............. 204/466; 204/616; 204/456; 204/606; 435/288.4

(58) Field of Classification Search ........ 204/456–467, 204/606–620; 435/288.4, 288.5, 305.2
See application file for complete search history.

(56) References Cited

U.S. PATENT DOCUMENTS

| | | | |
|---|---|---|---|
| 3,062,731 A | 11/1962 | Durrum | |
| 3,715,295 A | 2/1973 | Toccl | |
| 3,764,513 A | 10/1973 | Saravis | |

(Continued)

FOREIGN PATENT DOCUMENTS

EP        155 977        10/1985

(Continued)

OTHER PUBLICATIONS

Computer translation of JP 2000-060554.

(Continued)

*Primary Examiner*—Alex Noguerola
(74) *Attorney, Agent, or Firm*—Castellano Malm Ferrario & Buck PA (57) ABSTRACT

The present invention includes apparatus for simultaneous loading of multiple samples for molecular separation, including a separation area with walls wherein at least one of the walls has apertures having loading sites, a gel located within the separation area, and a plurality of wells within the gel. The apertures are connected to the plurality of wells by channels structurally configured to convey samples from the apertures to the wells.

The present invention further includes apparatus for electrophoresis separation having a substantially closed electrophoresis area, an electrophoresis gel located within the electrophoresis area, and multiple rows of wells within the electrophoresis gel, wherein the rows are arranged in a stagger format.

A device is provided for delivering samples into wells for molecular separation, having a flat surface with a top side and a bottom side, multiple loading sites on the top side arranged in standard format, multiple apertures on the bottom side arranged in stagger format and leading to the wells, and a channel through the flat surface connecting the loading sites to the apertures.

The present invention provides a method for simultaneous loading of multiple samples into an electrophoresis apparatus, including the steps of providing an electrophoresis apparatus having an area with walls defining the area and a gel within the area having multiple wells arranged in stagger format, wherein the walls include apertures having loading sites and channels structurally configured to direct samples into the wells, loading the samples into the loading sites with a standard multiple loading mechanism, and conveying the samples from the loading sites to the wells.

39 Claims, 4 Drawing Sheets

U.S. PATENT DOCUMENTS

| | | | |
|---|---|---|---|
| 4,018,662 | A | 4/1977 | Ruhenstroth-Bauer et al. |
| 4,130,471 | A | 12/1978 | Grunbaum |
| 4,219,395 | A | 8/1980 | Smith et al. |
| 4,305,799 | A | 12/1981 | Schwarz et al. |
| 4,323,439 | A | 4/1982 | O'Farrell |
| 4,874,491 | A | 10/1989 | Stalberg |
| 4,892,639 | A | 1/1990 | Sarrine et al. |
| 5,006,473 | A | 4/1991 | Bouma et al. |
| 5,045,164 | A | 9/1991 | Tansamrit et al. |
| 5,082,548 | A | 1/1992 | Faupel et al. |
| 5,106,477 | A | 4/1992 | Coleman |
| 5,209,831 | A | 5/1993 | MacConnell |
| 5,407,552 | A | 4/1995 | Lebacq |
| 5,411,657 | A | 5/1995 | Leka |
| 5,464,516 | A | 11/1995 | Takeda et al. |
| 5,464,517 | A | 11/1995 | Hjerten et al. |
| 5,582,702 | A | 12/1996 | Cabilly et al. |
| 5,656,145 | A | 8/1997 | Nguyen et al. |
| 5,785,835 | A | 7/1998 | Saito et al. |
| 5,843,295 | A | 12/1998 | Steiner et al. |
| 5,865,974 | A | 2/1999 | Cabilly et al. |
| 5,972,188 | A | 10/1999 | Rice et al. |
| 6,013,166 | A | 1/2000 | Heller |
| 6,056,860 | A | 5/2000 | Amigo et al. |
| 6,068,752 | A | 5/2000 | Dubrow et al. |
| 6,071,396 | A | 6/2000 | Day |
| 6,096,182 | A | 8/2000 | Updyke et al. |
| 6,113,766 | A | 9/2000 | Steiner et al. |
| 6,232,076 | B1 | 5/2001 | Schulz |
| 6,379,516 | B1 | 4/2002 | Cabilly et al. |
| 2002/0112960 | A1 | 8/2002 | Cabilly et al. |
| 2002/0134680 | A1 | 9/2002 | Cabilly et al. |

FOREIGN PATENT DOCUMENTS

| | | |
|---|---|---|
| EP | 1 167 962 | 1/2002 |
| WO | WO 87/04948 | 8/1987 |
| WO | WO 94/08234 | 4/1994 |
| WO | WO 96/18891 | 6/1996 |
| WO | WO 96/34276 | 10/1996 |
| WO | WO 97/41070 | 11/1997 |
| WO | WO 98/10277 | 3/1998 |
| WO | WO 98/35013 | 8/1998 |
| WO | WO 00/16084 | 3/2000 |
| WO | WO 02/18901 | 3/2002 |
| WO | WO 02/071024 | 9/2002 |

OTHER PUBLICATIONS

Abstract of JP 362066153.

A.T. Andrews, "Electrophoresis: Theory, Techniques and Bio-Chemical and Clinical Applications", Chapter 1, Clarendon press, Oxford 1993.

A.T. Andrews, "Electrophoresis: Theory, Techniques and Bio-Chemical and Clinical Applications", p. 79, 2nd Edition, 1986.

Stoyanov A.V. et al., "Properties of buffer-systems with charges immobilized on a get matrix and their potential use in capillary electrophoresis", Journal of Chromatography A, Elsevier Science, NL, vol. 799, No. 1-2, Mar. 13, 1998, pp. 275-282.

Weber G. et al., "Optimized continuous flow electrophoresis", Electrophoresis, Weinheim, DE, vol. 17, No. 12, 1996, pp. 1906-1910.

European Search Report for EP 02 702692, mailed Aug. 2, 2004.

ELECTROPHORESIS APPARATUS FOR SIMULTANEOUS LOADING OF MULTIPLE SAMPLES

CROSS-REFERENCE TO RELATED APPLICATIONS

This application is CONTINUATION of U.S. patent application Ser. No. 09/651,087, filed Aug. 30, 2000, now U.S. Pat. No. 6,562,213, which is incorporated herein by reference in its entirety for all purposes.

FIELD OF THE INVENTION

The present invention provides an apparatus for simultaneously loading multiple samples for conducting an electrophoresis test.

BACKGROUND OF THE INVENTION

A great deal of diagnostic procedures and laboratory research are carried out wherein DNA, RNA or proteins are separated according to their physical and chemical properties via electrophoresis. This process is widely used and has many applications. For example, electrophoresis is used to analyze DNA molecules according to their resultant size after being digested by restriction enzymes. It is also used to analyze the products of a polymerase chain reaction (PCR).

In some instances, molecules are driven toward a capture layer, which has part of a molecular recognition pair e.g. antibody-antigen, DNA-DNA probe, biotin-avidin, ligand-receptor, lectin-carbohydrate or others. Only specific parts of each pair of molecules that move through the capture layer are captured (e.g., an antigen when the capture layer contains a specific antibody), while the non-specific molecules pass through the layer unimpeded.

Electrophoresis separation is carried out in a separation medium, such as a gel of agarose or acrylamide or a combination of the two. Agarose gels are cast in open trays and form a horizontal slab whereas acrylamide gels are vertically cast between two glass plates.

Prior to electrophoresis separation, wells are introduced into the gel for sample deposition by applying a comb-like structure prior to the solidification or polymerization of the gel matrix. A row of approximately 8–15 wells is formed across one end of the gel.

In order to effect the electrophoresis separation, two opposite ends of the gel are exposed to a buffered solution which is connected by electrodes, often made of platinum, to an electrical power source. Once the electrical power source is switched on, the electric field forces negatively charged molecules to move towards the anode and positively charged molecules to move towards the cathode. DNA is negatively charged and therefore, in the agarose or acrylamide gels which provide sieving action, DNA molecules move towards the anode at a rate which depends on their size, wherein the smaller the molecules the faster they move. The running distance should be long enough to allow sufficient differentiation between molecules.

It is desirable to visualize and to document the results of the electrophoresis separation test. In electrophoresis separation of DNA molecules, this has been done by immersing the gel slab after the electrophoresis separation has been completed in a solution of a fluorescent compound, such as ethidium bromide, which intercalates within DNA molecules and emits visible light when exposed to an ultraviolet (UV) light. In order to document the results, a picture of the gel is taken through one of various photographic means.

Prior art electrophoresis systems are potential sources of contamination to the working environment in which the tests are performed. The two major sources of contamination are ethidium bromide and PCR products. Ethidium bromide is a hazardous chemical due to its mutagenic activity and therefore, exposure to ethidium bromide may induce malignant tumors. PCR is an extremely sensitive method to the extent that a single molecule of DNA product from one PCR (out of the trillions of molecules being produced) may interfere with the subsequent PCR such that it will produce incorrect results.

Also, conventional electrophoresis is time consuming in terms of preparation and handling. This is particularly true when a large number of samples are to be analyzed, and loading of samples is done one by one.

Several inventions have been directed towards eliminating contamination, such as U.S. Pat. No. 5,972,188, which describes the use of a membrane loader for gel electrophoresis; and an electrophoresis apparatus with a cover, in U.S. Pat. Nos. 5,582,702, and 5,865,974 incorporated herein by reference. The apparatus is directed towards the running of electrophoresis separation, as well as detecting and analyzing the results, within a self-contained, disposable unit.

Attempts have been made to reduce the time it takes to run an electrophoresis separation as well by loading many samples at once. Further, simultaneous loading of samples could reduce contamination and human error. Standards in cell culture, ELISA and PCR analysis provide different sized plates, with corresponding pipettes for ease in sample loading and analysis. For example, 96-well plates are typically used. Correspondingly, pipettes that fit this configuration are available and are widely used. Use of standard microtiter pipettes would greatly reduce the loading time for electrophoresis.

Saito et al., in U.S. Pat. No. 5,785,835, address this issue by providing an apparatus for loading of samples into wells within an exposed gel with standard pipettes. However, the testing apparatus has limited resolution capacity since a running distance of only 0.8 cm is available. In U.S. Pat. No. 6,071,396 a gel-matrix layer is described with wells arranged for loading of samples with standard pipettes. In this patent, the running distance is increased by diagonally offsetting the entire array of wells. U.S. Pat. No. 6,013,166 describes a method for reducing the linear dimension necessary for electrophoresis separation in a micro-gel format.

In addition, several needle guide designs have been developed to aid in loading samples directly into wells in a way that would save time and prevent inaccuracies. For example, U.S. Pat. No. 5,656,145 provides a needle guide for loading samples into a vertical slab gel. Similarly, U.S. Pat. No. 5,843,295 is directed towards a combination comb/loading guide unit. In both of these designs, the loading sites are positioned directly on top of the wells so as to allow for simple, direct loading of samples.

SUMMARY OF THE INVENTION

This invention provides, in accordance with an embodiment of the present invention, an apparatus for simultaneous loading of multiple samples for molecular separation, including a separation area with walls wherein at least one of the walls has multiple apertures with loading sites, a gel located within the separation area, and a plurality of wells within the gel. The apertures are connected to the plurality of wells by channels structurally configured to convey samples from the apertures to the wells. In one embodiment, the loading sites are spaced at predetermined intervals so as to conform with intervals between tips on a loader.

In one embodiment, the plurality of wells is arranged in rows, and the rows are arranged in stagger format, providing a running distance for molecular separation which is longer than the distance between two adjacent rows.

There is provided, in accordance with another embodiment of the present invention an apparatus for electrophoresis separation having a substantially closed electrophoresis area, an electrophoresis gel located within the electrophoresis area, and multiple rows of wells within the electrophoresis gel, wherein the rows are arranged in a stagger format.

There is provided, in accordance with another embodiment of the present invention, a gel layer for molecular separation having a plurality of wells within the gel layer. The wells are arranged in a plurality of rows, and wells of one row are horizontally shifted from wells of a neighboring row by a predetermined distance. The horizontal shift is alternated from left to right, so as to form a staggered format of wells within the gel layer.

There is provided, in accordance with another embodiment of the present invention a device for delivering samples into wells for molecular separation, having a flat surface with a top side and a bottom side, multiple loading sites on the top side arranged in standard format, multiple apertures on the bottom side arranged in stagger format and leading to the wells, and a channel through the flat surface connecting the loading sites to the apertures.

There is provided, in accordance with another embodiment of the present invention an electrophoresis apparatus for non-weighted sample deposition, including a substantially closed area, an electrophoresis gel with wells located within the electrophoresis area, and a non-liquid ion source located within the gel, eliminating the need for weighting samples before deposition into the wells.

There is provided, in accordance with another embodiment of the present invention a system for conducting electrophoresis separation including an electrical power source, a substantially closed disposable cassette for conducting an electrophoresis separation therein and having conductive elements therein, and a support for supporting the substantially closed cassette and for connecting the electrical power source to the conductive elements of the cassette, where one or more gels may be connected simultaneously. The cassette includes a body of gel for carrying therein the electrophoresis separation, a plurality of wells in the body of gel arranged in a stagger format and a plurality of apertures having loading sites leading to the plurality of wells.

There is provided, in accordance with another embodiment of the present invention a method for treating water-absorbent plastic used for electrophoresis devices, including the steps of placing the water-absorbent plastic in a humidified environment and saturating the water-absorbent plastic by leaving it in a humidified environment for a predetermined period of time.

There is provided, in accordance with another embodiment of the present invention a method for simultaneous loading of multiple samples into an electrophoresis apparatus, including the steps of providing an electrophoresis apparatus having an area with walls defining the area and a gel within the area having multiple wells arranged in stagger format, wherein the walls include apertures having loading sites and channels structurally configured to direct samples into the wells, loading the samples into the openings with a standard multiple loading mechanism, and directing the samples from the apertures to the wells.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
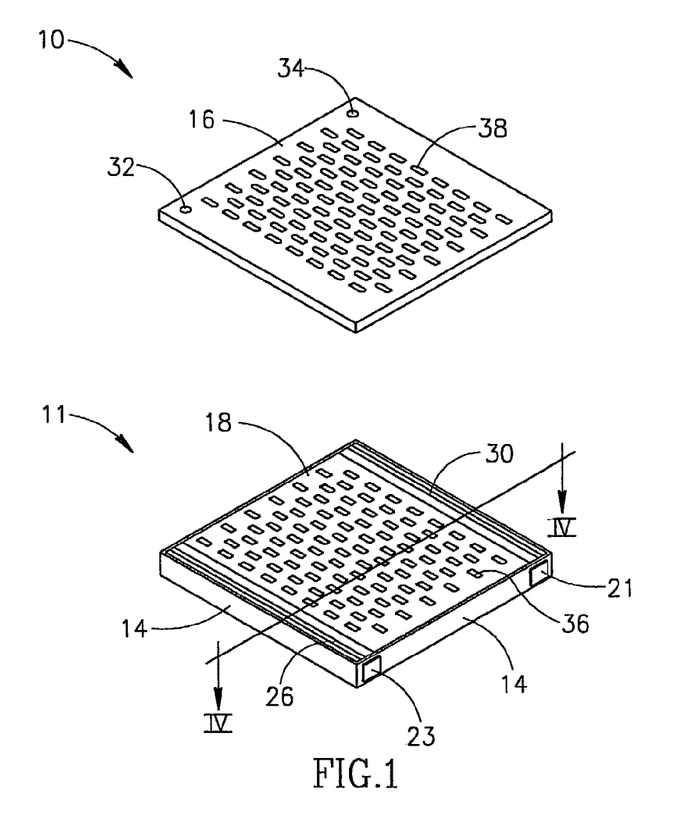
FIGS. 1 and 2 are schematic illustrations of an electrophoresis apparatus in accordance with an embodiment of the present invention.
Figure 2:
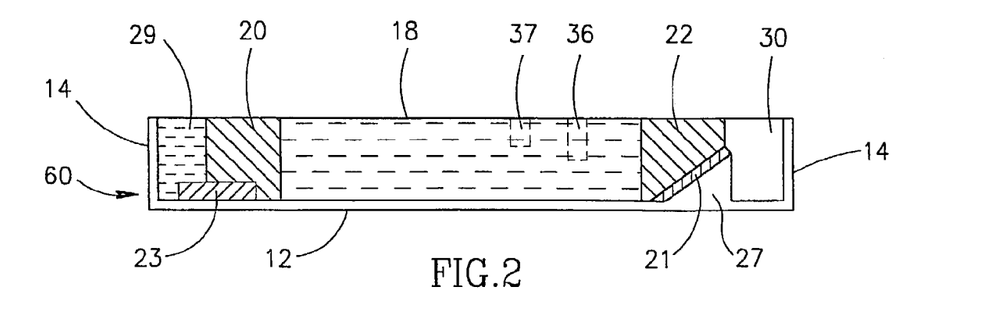

Reference is made to FIGS. 1 and 2, which illustrate an electrophoresis disposable cassette, generally referenced 10. FIG. 1 shows an external configuration of cassette 10, while FIG. 2 shows a cross-sectional view. Cassette 10 is a closed disposable cassette used for a single electrophoresis test, and includes all the chemical compounds required for driving the electrophoresis separation and for enabling visualization of its results when DNA as well as RNA or protein molecules have been separated, as will be described hereinbelow.

As shown in FIG. 1, cassette 10 comprises a three dimensional separation area 11 having bottom wall and side walls, referenced 12 and 14 respectively, and a top wall 16 having a specified thickness. Cassette 10 is substantially closed in that it is enclosed by walls 12, 14 and 16, but it also comprises vent holes and apertures as will be described hereinbelow. In one embodiment, the thickness ranges from 0.1–10 mm. In another embodiment, the thickness is 1.5 mm. Cassette 10 as shown in FIG. 1 has a specified length, width and height. In one embodiment, the length ranges from 100–200 mm, the width ranges from 50–150 mm and the height ranges from 1–10 mm. In a preferred embodiment, length, width and height are 160 millimeters (mm), 100 mm and 6 mm, respectively. In another preferred embodiment, length, width and height are 130 mm, 130 mm and 6 mm, respectively.

Bottom wall 12 and top wall 16 are preferably made of any suitable UV transparent material, such as the TPX plastic commercially available from MITSUI of Japan or the Polymethylmethacrylate (PMMA) plastic commercially available from Repsol Polivar S.P.A. of Rome, Italy. Cassette 10 may include vent holes 32 and 34 to allow for gaseous molecules that might be generated due to the electrochemical reaction (e.g., oxygen and/or hydrogen) to be released. In one embodiment, vent holes range in diameter from 0.5–2 mm. In a preferred embodiment, vent holes are 1 mm in diameter.

As seen in the cross section illustration (IV—IV) of FIG. 2, area 11 comprises a gel matrix 18 which may be any suitable gel matrix for electrophoresis, such as an agarose gel or a gel made of acrylamide (available from, for example, Sigma, St. Louis, Mo., USA). A plurality of wells 36 may be introduced into gel 18, by using a "comb" having a row of protruding teeth positioned so that the teeth project into the gel layer while it sets. In one embodiment, the plurality of wells ranges from 1–200 wells. In another embodiment, the plurality of wells ranges from 8–12 wells. In another embodiment, the plurality of wells includes 96 wells.

When the gel has set, the comb is removed to leave a row of wells 36, or holes, in the layer. In one embodiment, wells 36 are dimensions of 0.5–5 mm wide, 1–5 mm long, and 3–5 mm deep, and are used to introduce samples of the molecules to undergo molecular separation. One row or several rows may be formed. In one embodiment of the present invention, 12 rows of 8 wells per row are formed, and are arranged in a stagger format, as shown in FIG. 1 and described more fully below. In another embodiment, 8 rows of 12 wells per row are formed and may also be arranged in a stagger format. For one embodiment of the present invention, top wall 16 has apertures used as loading sites 41, as described more fully below.

In addition, cassette 10 may optionally include a capture layer 37 including part of a molecular recognition pair for separating samples according to binding properties. Capture layer 37 is immobilized within gel 18, and is fabricated with resins to which the binding site of a molecule of interest will covalently bind. Some examples include avidin on acrylic beads, biotin on cross linked beaded agarose and others. The resins are mixed with agarose or other materials and poured as layers into gel 18. Alternatively, acrydite™ (available from Mosaic Technologies, Waltham, Mass., USA) may be used. Acrydite™ is a phosphoramide that is capable of copolymerization with acrylamide, and it can be used to introduce copolymerizable groups on the 5' terminus of any oligonucleotide probe. To make the capture layer, Acrydite™ oligonucleotide capture probes may be mixed with acrylamide solutions and polymerized into gel layers.

The capture electrophoresis technique provides concentrated signals, saves time and saves material. One or multiple capture layers may be used. This technique may be performed on its own, or in combination with a standard size electrophoresis separation.

It is desirable to visualize and to document the results of the electrophoresis separation test. In electrophoresis separation of DNA molecules, this has been done by immersing the gel slab after the electrophoresis separation has been completed in a solution of a fluorescent compound which emits visible light when exposed to an ultra violet (UV) light. According to one embodiment of the present invention, the samples or the gel interact with ethidium bromide or other fluorescent dyes. In this way, the results may be viewed in situ, without the need for exposing the samples to contamination by removing the gel from the enclosed area 11.

According to another embodiment of the present invention, various types of light sources may be used. In one embodiment, a light source of adjustable or non-adjustable wavelengths may be used. The light source may include visible or non-visible light.

Alternatively a colorimetric dye, such as Methylene Blue may be added to the samples, the gel, or the ion reservoir and may interact with the molecules undergoing electrophoresis separation, so as to enable visualization of the results without the need for a UV light source.

Area 11 also comprises two conductive electrodes referenced 21 and 23 which, when connected to an external direct current (DC) electrical power source, provide the electric field required to drive electrophoresis separation. In the illustrated embodiment, electrode 21 is the cathode and electrode 23 is the anode. The system may also include a support for connecting conductive elements of cassette 10 to the power source. In one embodiment, the support is configured to connect to one or more gels simultaneously. Further, the system optionally includes a camera for documentation.

In one embodiment, the gel 18 and the conductive electrodes 21 and 23 are in contact with non-liquid ion sources such as ion exchange matrices as described in U.S. Pat. Nos. 5,582,702 and 5,865,974.

It should be noted that since plastics used as cassette material are sometimes water absorbent, they may be pretreated by placement in a humidified environment and saturation by leaving it for a predetermined period of time so as to avoid later water adsorption or uptake of liquid, thereby keeping the gel intact. In one embodiment, the period of time ranges from 1–72 hours. In another embodiment, the period of time ranges from 1–20 days. In another embodiment, the period of time is at least 10 days. In a preferred embodiment, the period of time is 10 days.

It should be noted that in conventional electrophoresis, samples must be weighted so that they sink through the buffer to the bottom of the wells. This is generally accomplished by combining a substance such as Glycerol, Sucrose, or Ficoll polymer with the sample. It will be appreciated that in one embodiment of the present invention, there is no liquid buffer present in the vicinity of the wells, and instead, a non-liquid ion source is located within said gel. Thus, the step of weighting samples before deposition into said wells may be eliminated, thereby decreasing the time necessary to perform an experiment.

Figure 3A:
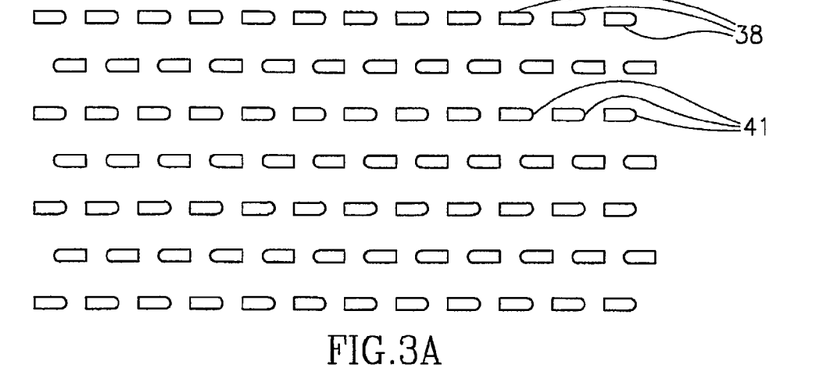
FIGS. 3A–3D are geometric illustrations of configurations of wells and apertures and loading sites according to one embodiment of the present invention.
Figure 3B:
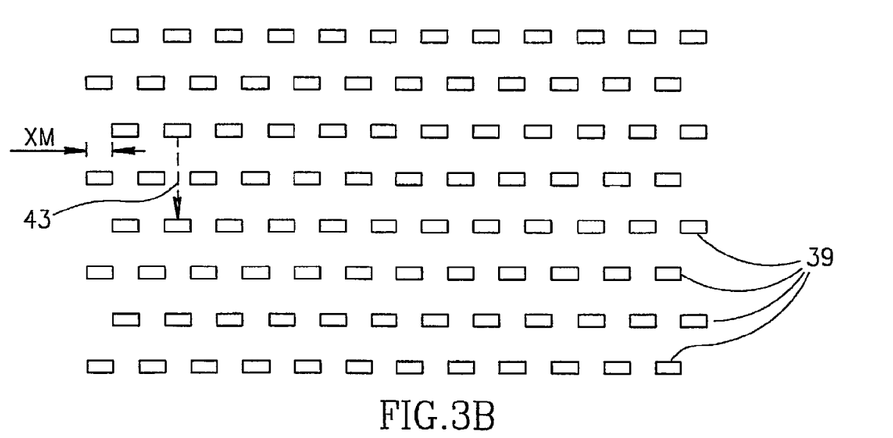
Figure 3C:
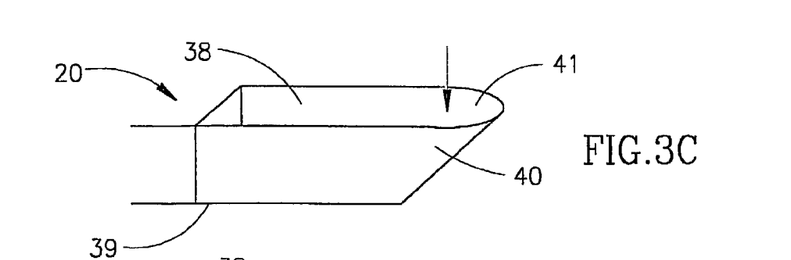
Figure 3D:
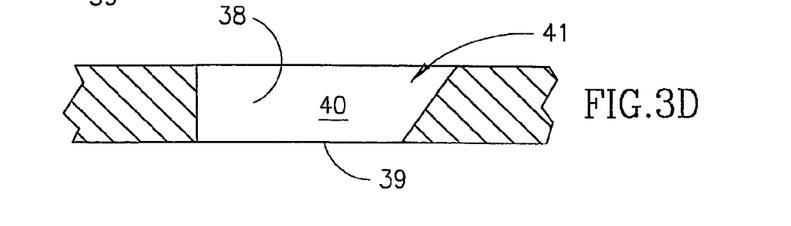
Figure 4A:
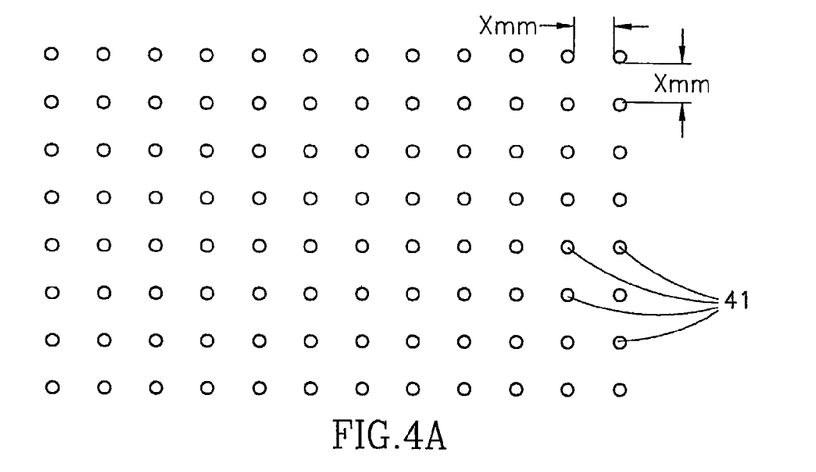
FIGS. 4A–4C are geometric illustrations of configurations of wells and apertures and loading sites according to another embodiment of the present invention.
Figure 4B:
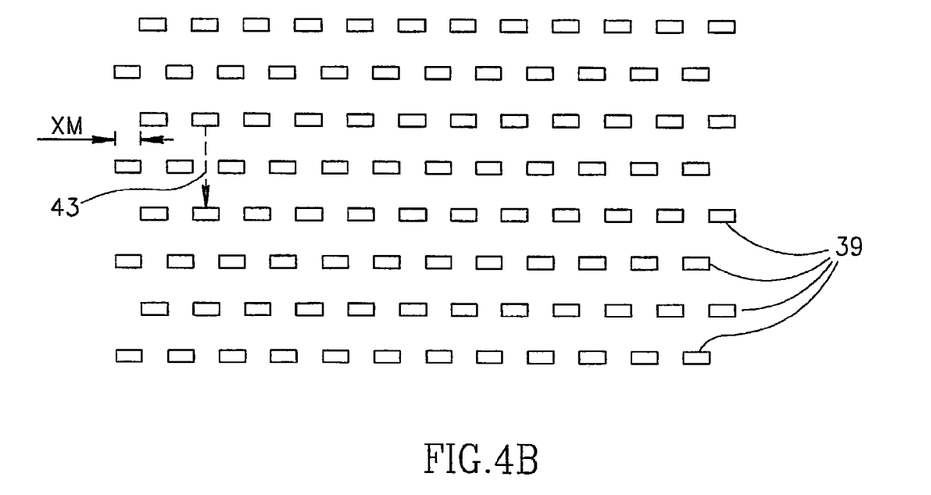

Reference is now made to FIGS. 3A–3D, taken together with 4A–4C, which show embodiments of loading sites 41 and outlet apertures 39 on two sides of wall 16. It will be appreciated that in one embodiment, wall 16 refers to the top wall, or the cover, of the apparatus. In another embodiment, other walls are used, such as side walls. Wall 16 should be considered as a flat surface with a top side and a bottom side. FIGS. 3A and 4A show views from the top side of wall 16. FIGS. 3B and 4B show views from the bottom side of wall 16. FIG. 3C shows a three-dimensional view of a portion of wall 16. FIGS. 3D and 4D show cross-sectional views of a portion of wall 16.

Stagger format of outlet apertures 39, located on the bottom side of wall 16, corresponds to stagger format of wells 36 within a layer of gel 18, as depicted in FIGS. 3B and 4B. That is, wells of one row are horizontally shifted from wells of a neighboring row by a predetermined distance. In one embodiment, the predetermined distance is in the range of 0.05–20 mm. In another embodiment, the predetermined distance is 4.5 mm. The horizontal shift occurs in alternating directions from left to right, so as to form a staggered format.

Thus, when electrophoresis separation takes place, the available running distance between adjacent wells 36 in the direction of electrophoresis separation is from 8–20 mm. In one embodiment, the available running distance is up to 18 mm, as shown by arrow 43. This amount is double what would be available without stagger formatting, greatly increasing the potential for larger sized molecules to be separated. If wells 36 were arranged according to a standard format, and not a stagger format, samples in each row would have a running distance of less than 1 cm, whereas in the configuration illustrated in FIG. 3B, twice that distance is available since samples can run between wells 36 of the next row.

In the embodiment shown in FIG. 3A, inlet apertures 38 have loading sites 41 located on the edges, all on the top of wall 16 of cassette 10. Loading sites 41 are configured either linearly (one row), or in a geometrical arrangement of columns and rows, typically in a rectangular arrangement. In one embodiment, loading sites 41 are spaced at predetermined intervals so as to conform with intervals between tips on a loader. "Loader" refers to a mechanism used to load samples, such as a micro-titer pipette, as described hereinbelow. Multiple loading mechanisms allow for many samples to be loaded at once. Thus, the spacing between loading sites can vary, and may be configured to conform with intervals on any type of loader. In one embodiment, the predetermined intervals include 0.5–2 mm spacings. In a preferred embodiment, the predetermined intervals include 9 mm spacings, so as to conform with a micro-titer multi-pipette loader for 96 wells. In another embodiment, predetermined intervals include 0.001–1 mm spacings, so as to allow for a micro-scale system.

The shape of loading sites 41 may vary, but they are typically circular, so as to fit the end of a loader tip. A standard multiple loading mechanism such as a micro-titer multi-pipette loader available from, for example, Eppendorf Scientific, Inc., Westbury, N.Y., USA may be used, thus enabling simultaneous loading of as many samples as can fit in the pipette. Thus, for a 96-well configuration, loaders are available from, for example, Beckman Coulter, Inc., Fullerton, Calif., USA, that would enable loading of 96 samples all at the same time, or loading of 8 or 12 samples at a time. Similar models might be available for the other formats as well.

Loading sites 41, either located on the edges of inlet apertures 38 as in FIG. 3A, or alone, as in FIG. 4A, are not directly above outlet apertures 39, which lead into wells 36. Therefore, samples must be conveyed to wells 36, either by use of an incline, or by some other method, as described hereinbelow. Variations of the described embodiments are possible, for example, apertures and loading sites located in walls other than wall 16, such as side walls which in a vertical gel would form the top wall.

Figure 4C:
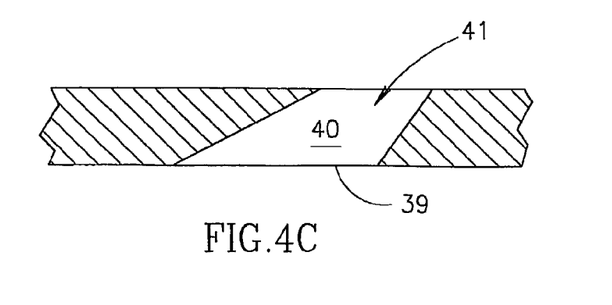

As shown in FIGS. 3D and 4C, channels 40 connect loading sites 41 to outlet apertures 39. Channels 40 are formed from structural adaptations of wall 20 connecting loading site 41 to outlet aperture 39 so as to allow for the flow of a sample from loading site 41 to outlet aperture 39. Channels 40 are structurally configured in such a way so as to convey samples into wells 36. In one embodiment, channel 40 comprises an incline. In another embodiment, channel 40 comprises another feature to help convey the sample, such as a magnetic or electrical property.

Figure 5:
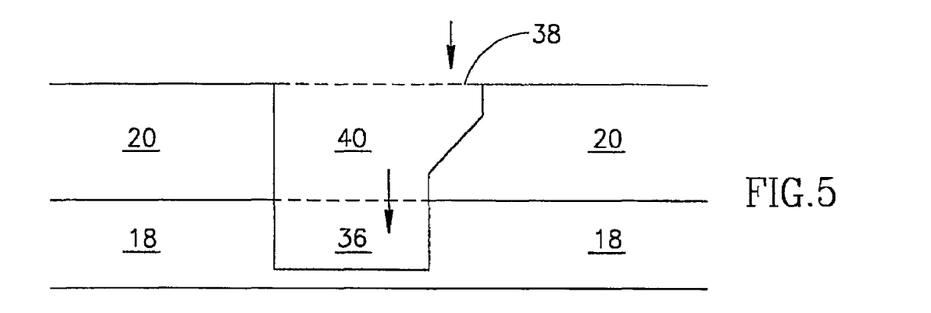
FIG. 5 is a schematic illustration of a channel configuration in accordance with one embodiment of the present invention.

Reference is now made to FIG. 5, which shows an embodiment of the present invention. A wide loading site 41 is portrayed above outlet aperture 39. Thus, the shape and/or size of loading site 41 differs from the shape and/or size of outlet aperture 39. In this example, channel 40 is configured in an irregular shape so as to allow for the sample to be directed into outlet aperture 39, even though application of the sample may not occur directly in line With outlet aperture 39.

Figure 6:
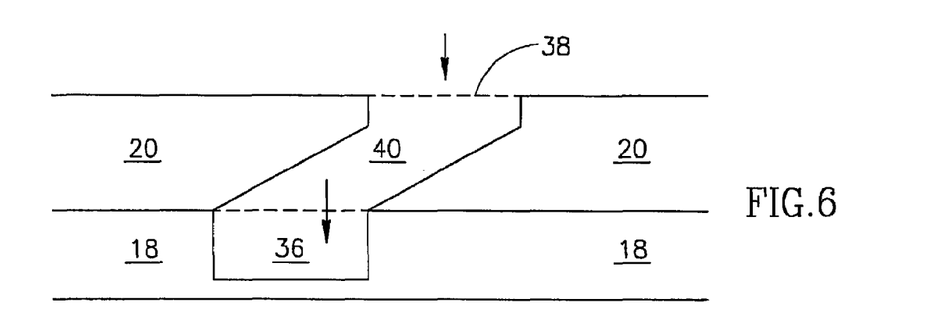
FIG. 6 is a schematic illustration of a channel configuration in accordance with another embodiment of the present invention.

Reference is now made to FIG. 6, which shows a further embodiment of the present invention. Outlet aperture 39 and loading site 41 are indirectly aligned with one another. Since loading site 41 is not located directly above outlet aperture 39, an incline in channel 40 provides direction of the sample into outlet aperture 39, and then into well 36.

Figure 7A:
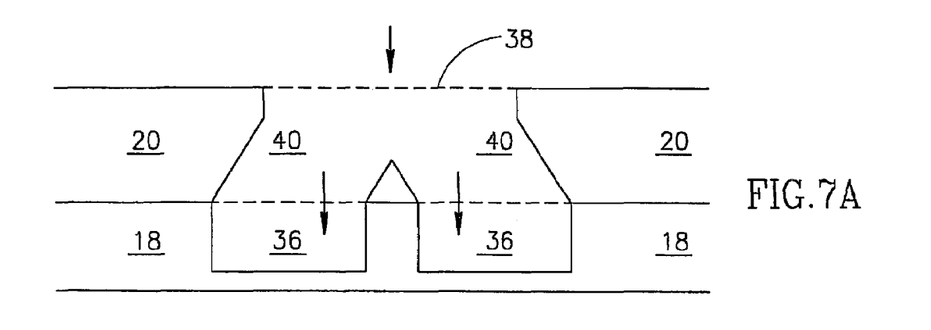
FIGS. 7A and 7B are schematic illustrations of channel configurations in accordance with further embodiments of the present invention.
Figure 7B:
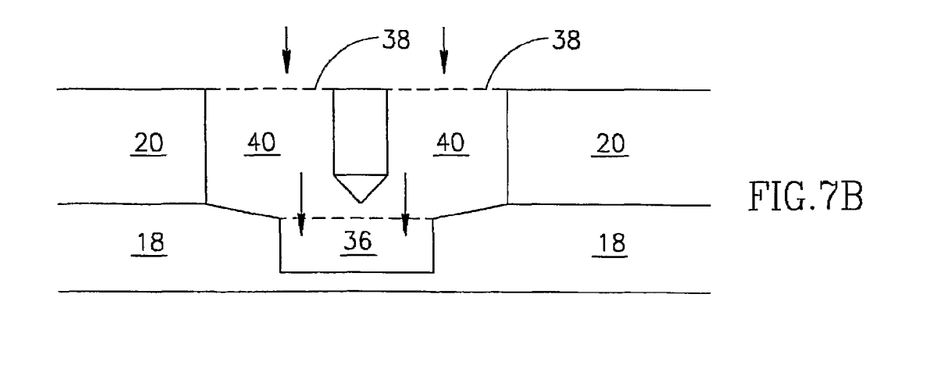

Reference is now made to FIGS. 7A and 7B, which are illustrations of further embodiments of the present invention. In FIG. 7A, one loading site 41 leads to multiple outlet apertures 39, and in FIG. 7B, multiple loading sites 41 lead to one outlet aperture 39. Thus, as shown in FIG. 7A, multiple tests can be performed on a sample after a single pipette application, reducing the sample loading time. This is accomplished by channel 40 having a branched configuration. Alternatively, if larger amounts of samples are needed, multiple amounts may be delivered to one well 36, as shown in FIG. 7B, without changing the settings on the pipettes. This, too, is accomplished by a structural channel 40 configuration. Many other configurations are possible.

It will be appreciated that the embodiments described hereinabove are described by way of example only and that numerous modifications thereto, all of which fall within the scope of the present invention, exist. For example, gels may be either vertical or horizontal. In addition, apertures may be on the side wall of the apparatus, rather than directly on the top cover. In one embodiment, the entire system is in a microscale range, in which case all the dimensions described hereinabove are reduced by a factor of 10–100.

It will be appreciated by persons skilled in the art that the present invention is not limited to what has been particularly shown and described hereinabove. Rather, the scope of the present invention is defined only by the claims that follow:

What is claimed is:

1. An apparatus for simultaneous loading of multiple samples for molecular separation, the apparatus comprising:
    a separation area having walls, wherein at least one of said walls comprises multiple apertures having loading sites;
    a gel located within said separation area; and
    a plurality of wells within said gel, wherein said apertures are connected to said plurality of wells by channels structurally configured to convey samples from said apertures to said wells, wherein said apertures are structurally different from said wells, and wherein said structural difference is selected from a difference in shape and a difference in alignment positions.

2. An apparatus for simultaneous loading of multiple samples for molecular separation, the apparatus comprising:
    a separation area having walls, wherein at least one of said walls comprises multiple apertures having loading sites;
    a gel located within said separation area; and
    a plurality of wells within said gel,
wherein said apertures are connected to said plurality of wells by channels structurally configured to convey samples from said apertures to said wells, wherein the channel configuration is selected from a channel configuration including an incline, a branched channel configuration, and a channel configuration including an irregular shape.

3. An apparatus for electrophoresis separation, the apparatus comprising:
    a substantially closed electrophoresis area;
    an electrophoresis gel located within said electrophoresis area;
    a wall in contact with said gel, said wall comprises a plurality of inlet apertures having loading sites located on a first side of said wall and multiple outlet apertures located on a second side of said wall, said wall comprises multiple channels therein connecting said inlet apertures with said outlet apertures; and multiple rows of wells within said electrophoresis gel, wherein at least three rows of said multiple rows are arranged in an alternating staggered format such that at least the first well of the second row of said at least three rows is laterally offset in a first direction along the axis of said second row relative to the position of the first well of the first row of said at least three rows along the axis of said first row, and wherein at least the first well of at least the third row of said at least three rows is laterally offset in a second direction opposite said first direction along the axis of said at least third row relative to the position of said first well of said second row along the axis of said second row.

4. The apparatus according to claim 3, wherein said outlet apertures open into said wells.

5. The apparatus according to claim 3, wherein said loading sites are arranged in non-staggered rows of loading sites configures to form at least two columns of loading sites.

6. The apparatus according to claim 3 wherein said loading sites are arranged in predetermined intervals.

7. The apparatus according to claim 6 wherein said predetermined intervals comprise loading site spacings in the range of 0.001–20 millimeters.

8. The apparatus according to claim 6 wherein said predetermined intervals comprise loading site spacings of 9 millimeters.

9. The apparatus according to claim 3, wherein said wall forms part of a substantially closed cassette, said cassette contains said gel therewithin, said cassette also includes electrically conducting elements for performing said electrophoresis separation.

10. A gel layer for molecular separation having a plurality of wells within said gel layer, wherein said wells form a plurality of spaced apart rows arranged in an alternating staggered format, wherein the wells of the odd rows are laterally offset by a predetermined distance in the same direction along the axes of said odd rows relative to the positions of the corresponding wells of the even rows along the axes of said even rows.

11. The gel layer according to claim 10 wherein said molecular separation is selected from the group consisting of electrophoresis separation by size, molecular separation by binding and a combination thereof.

12. The gel layer according to claim 10 wherein said predetermined distance is in the range of 0.0005–10 millimeters.

13. The gel layer according to claim 10 wherein said predetermined distance is 4.5 millimeters.

14. The gel layer according to claim 10 wherein the distance between the wells in a row of said rows is in the range of 0.001–20 millimeters.

15. The gel layer according to claim 10 wherein the distance between the wells in a row of said rows is 9 millimeters.

16. A device for delivering samples into sample wells formed in a gel for molecular separation, the device comprising:

a wall having a top side and a bottom side;

a plurality of inlet apertures formed in said top side, each inlet aperture of said plurality of inlet apertures comprises a loading site, the loading sites of said inlet apertures are arranged in non-staggered rows of loading sites configured to form at least two columns of loading sites;

a plurality of outlet apertures formed in said bottom side, said outlet apertures are configured to open into said wells when said wall is disposed in contact with said gel, said outlet apertures are arranged in a plurality of rows, at least three rows of said plurality of rows are arranged in an alternating staggered format such that at least the first outlet aperture of the second row of said at least three rows is laterally offset in a first direction along the axis of said second row relative to the position of the first outlet aperture of the first row of said at least three rows along the axis of said first row, and wherein at least the first outlet aperture of at least the third row of said at least three rows is laterally offset in a second direction opposite said first direction along the axis of said at least third row relative to the position of said first outlet aperture of said second row along the axis of said second row; and a plurality of hollow channels formed within said wall, each channel of said plurality of channels fluidically connects at least one inlet aperture to at least one outlet aperture of said plurality of outlet apertures for conveying fluid samples from said loading sites to said sample wells.

17. The device according to claim 16 wherein said wall is a top wall configured for covering said gel.

18. The device according to claim 16 wherein said loading site is formed as part of said inlet aperture and wherein the area of said loading site is smaller than the area of said inlet aperture.

19. The device according to claim 16 wherein said loading site comprises the entire area of said inlet aperture.

20. The device according to claim 16 wherein at least some channels of said plurality of channels fluidically connect a single inlet aperture of said plurality of inlet apertures to a single outlet aperture of said plurality of outlet apertures.

21. The device according to claim 16 wherein at least some channels of said plurality of channels fluidically connect two or more inlet apertures of said plurality of inlet apertures to a single outlet aperture of said plurality of outlet apertures.

22. The device according to claim 16 wherein at least some channels of said plurality of channels fluidically connect a single inlet aperture of said plurality of inlet apertures to two or more outlet apertures of said plurality of outlet apertures.

23. The device according to claim 16 wherein said loading sites are arranged in predetermined intervals.

24. The gel layer according to claim 23 wherein said predetermined intervals comprise loading site spacings in the range of 0.001–20 millimeters.

25. The device according to claim 23 wherein said predetermined intervals comprise loading site spacings of 9 millimeters.

26. The device according to claim 16 wherein said alternating staggered format of said plurality of outlet apertures conforms with an alternating staggered format of said sample wells of said gel.

27. The device according to claim 16 wherein said channels of said plurality of channels are selected from channels having an incline, channels having a branched configuration and channels having an irregular shape.

28. A method for molecular separation, the method comprising the steps of:

providing an apparatus having a separation area having at least a top wall defining a separation chamber and a gel within said chamber having multiple wells arranged in a plurality of rows, at least three rows of said plurality of rows are arranged in an alternating staggered format such that at least the first well of the second row of said at least three rows is laterally offset in a first direction along the axis of said second row relative to the position of the first well of the first row of said at least three rows along the axis of said first row, and wherein at least the first well of at least the third row of said at least three rows is laterally offset in a second direction opposite said first direction along the axis of said at least third row relative to the position of said first well of said second row along the axis of said second row, wherein said top wall comprises apertures having loading sites and channels structurally configured to direct samples into said wells;

loading said samples into said loading sites with a standard multiple loading mechanism;

directing said samples from said loading sites to said wells;

providing an electrical current through said separation area so as to allow for separation of said samples; and separating said samples according to predefined properties, wherein said predefined properties are selected from molecular size, binding properties, and a combination of molecular size and binding properties.

29. An apparatus for simultaneous loading of multiple samples for molecular separation, the apparatus comprising:

a gel having a plurality of wells therein, said wells are arranged in rows, at least three rows of said rows are alternating staggered rows of wells proving a running distance for said molecular separation which is longer than the distance between two adjacent rows of said at least three rows;

at least one wall in contact with said gel, said wall comprises multiple inlet apertures having loading sites, at least some loading sites of said multiple inlet apertures are arranged in non-staggered rows, at least two adjacent rows of said non-staggered rows are arranged to form at least two columns of loading sites, the loading sites of said at least two columns of loading sites are connected to the wells of said alternating staggered rows of wells by channels formed within said at least one wall and configured to convey samples from said loading sites to said wells.

30. The apparatus according to claim 29, wherein said plurality of wells of said gel comprises ninety six wells arranged in eight parallel rows, each of said rows includes twelve wells, wherein said eight rows are arranged in an alternating staggered configuration, and wherein said at least one wall is a top wall having ninety six inlet apertures having ninety six loading sites arranged in eight rows, each row of loading sites comprises twelve loading sites, wherein the spacing of said ninety six loading sites conforms with the spacing of the wells in a ninety six well microtiter plate.

31. The apparatus according to claim 29 wherein said plurality of wells of said gel comprises ninety six wells arranged in eight parallel rows, each of said eight rows includes twelve wells, wherein said eight rows are arranged in an alternating staggered configuration, and wherein said at least one wall is a top wall having ninety six inlet apertures having ninety six loading sites arranged in eight rows, each row of loading sites comprises twelve loading sites, wherein the spacing of said ninety six loading sites conforms with the spacing of the tips in a ninety six tip pipette suitable for simultaneous sampling of the wells of a ninety six well microtiter plate, to enable simultaneous loading of ninety six samples from said ninety six tip pipette into said ninety six wells of said gel.

32. The apparatus according to claim 29 wherein said at least one wall is part of a substantially closed cassette having a chamber therewithin, said gel is disposed within said chamber, wherein said cassette also comprises electrically conducting elements therein for performing said molecular separation.

33. The apparatus according to claim 29 wherein said gel comprises at least one substance selected from agarose, polyacrylamide and a mixture of agarose and polyacrylamide.

34. The apparatus according to claim 29 wherein the thickness of said gel is more than 2 millimeters.

35. An apparatus for simultaneous loading of multiple samples for molecular separation, the apparatus comprising:

a gel having a plurality of wells therein, said wells are arranged in rows, at least three rows of said rows are staggered rows of wells proving a running distance for said molecular separation which is longer than the distance between two adjacent rows of said at least three rows;

at least one wall having a first surface and a second surface, said second surface is in contact with said gel, said wall comprises multiple channels passing therethrough, each channel has at least one inlet aperture comprising a loading site opening at said first surface and at least one outlet aperture opening at said second surface, said at least one outlet aperture opens into at least one well of said wells, at least some loading sites of said multiple channels are arranged on said first surface in non-staggered rows, at least two adjacent rows of said non-staggered rows of loading sites are arranged to form at least two columns of loading sites, the loading sites of said at least two columns of loading sites are connected to the wells of said staggered rows of wells by said channels to convey samples from said loading sites to said wells.

36. The apparatus according to claim 35 wherein at least some channels of said multiple channels have two or more loading sites and a single outlet aperture.

37. The apparatus according to claim 35 wherein at least some channels of said multiple channels have a single loading site and two or more outlet apertures, each outlet aperture of said two or more outlet apertures opens into a different well of said wells.

38. The apparatus according to claim 35 wherein at least some channels of said multiple channels have a single loading site and two or more outlet apertures allowing the distributing of a single sample introduce through said single loading site into two or more wells through said two or more outlet apertures.

39. An apparatus for simultaneous loading of multiple samples for molecular separation, the apparatus comprising:

a gel having a plurality of wells therein, said wells are arranged in a plurality of rows of wells, wherein said plurality of rows are arranged in an alternating staggered row format for providing a running distance for said molecular separation which is longer than the distance between adjacent rows of said wells;

at least one wall in contact with said gel, said wall comprises multiple channels formed therein, said channels having loading sites, the loading sites of said multiple channels are arranged in non-staggered rows configured to form at least two columns of loading sites, the loading sites of said at least two columns of loading sites are fluidically connected to the wells of said staggered rows of wells by said channels and are configured to convey fluid samples from said loading sites to said wells.

* * * * *